US006902581B2

(12) United States Patent
Walkenhorst et al.

(10) Patent No.: US 6,902,581 B2
(45) Date of Patent: *Jun. 7, 2005

(54) APPARATUS FOR FUSING ADJACENT BONE STRUCTURE

(75) Inventors: Jared Walkenhorst, Fairfield, CT (US); Herb Cohen, Shelton, CT (US); Lance Middleton, Trumbull, CT (US)

(73) Assignee: Kowmedica Osteonics Corp., Mahwah, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/041,541

(22) Filed: Oct. 24, 2001

(65) Prior Publication Data

US 2002/0065559 A1 May 30, 2002

Related U.S. Application Data

(60) Provisional application No. 60/242,843, filed on Oct. 24, 2000.

(51) Int. Cl.$^7$ .................................................. A61F 2/44
(52) U.S. Cl. .................................................. 623/17.16
(58) Field of Search .......................... 623/17.16, 17.11; 606/61, 62, 72, 60

(56) References Cited

U.S. PATENT DOCUMENTS

| | | | |
|---|---|---|---|
| 4,349,921 A | 9/1982 | Kuntz | |
| 4,501,269 A | 2/1985 | Bagby | |
| 4,743,256 A | 5/1988 | Brantigan | |
| 4,834,757 A | 5/1989 | Brantigan | |
| 4,877,020 A | 10/1989 | Vich | |
| 4,878,915 A | 11/1989 | Brantigan | |
| 4,936,848 A | * 6/1990 | Bagby | 623/17.16 |
| 4,961,740 A | 10/1990 | Ray et al. | |
| 5,015,255 A | 5/1991 | Kuslich | |
| 5,026,373 A | 6/1991 | Ray et al. | |
| 5,171,278 A | 12/1992 | Pisharodi | |
| 5,390,683 A | 2/1995 | Pisharodi | |
| 5,443,514 A | 8/1995 | Steffee | |
| 5,458,638 A | 10/1995 | Kuslich et al. | |
| 5,489,308 A | 2/1996 | Kuslich et al. | |
| 5,534,031 A | 7/1996 | Matsuzaki et al. | |
| 5,653,761 A | 8/1997 | Pisharodi | |
| 5,653,762 A | 8/1997 | Pisharodi | |
| 5,658,336 A | 8/1997 | Pisharodi | |
| 5,658,337 A | 8/1997 | Kohrs et al. | |
| 5,665,122 A | * 9/1997 | Kambin | 623/17.16 |
| 5,669,909 A | 9/1997 | Zdeblick et al. | |
| 5,674,296 A | 10/1997 | Bryan et al. | |
| 5,766,253 A | 6/1998 | Brosnahan, III | |
| 5,782,919 A | 7/1998 | Zdeblick et al. | |
| 5,865,847 A | 2/1999 | Kohrs et al. | |
| 5,876,457 A | * 3/1999 | Picha et al. | 623/17.11 |

(Continued)

Primary Examiner—Kevin Shaver
Assistant Examiner—D. Austin Bonderer
(74) Attorney, Agent, or Firm—Lerner, David, Littenberg, Krumholz & Mentlik, LLP

(57) ABSTRACT

A fusion implant apparatus for facilitating fusion of adjacent bone structures includes a threadless implant member which is positioned between adjacent opposed bone structures. The implant member defines a longitudinal axis and first and second longitudinal ends and has an outer wall which is dimensioned to engage the opposed bone structures upon positioning therebetween in supporting relation therewith. The outer wall defines an internal cavity for the reception of bone growth inducing substances and includes a plurality of apertures which extend therethrough in communication with the internal cavity to permit fusion of vertebral bone tissue. The implant member also includes an intermediate portion which defines a cross-sectional dimension transverse to the longitudinal axis which is greater than the respective cross-sectional dimensions of the first and second longitudinal ends of the implant member.

18 Claims, 4 Drawing Sheets

U.S. PATENT DOCUMENTS

| | | | |
|---|---|---|---|
| 5,888,224 A | | 3/1999 | Beckers et al. |
| 5,895,427 A | | 4/1999 | Kuslich et al. |
| 5,906,616 A | | 5/1999 | Pavlov et al. |
| 5,968,098 A | | 10/1999 | Winslow |
| 6,059,829 A | * | 5/2000 | Schlapfer et al. ........ 623/17.16 |
| 6,080,158 A | | 6/2000 | Lin |
| 6,093,207 A | | 7/2000 | Pisharodi |
| 6,123,705 A | * | 9/2000 | Michelson ............... 623/17.16 |
| 6,165,219 A | | 12/2000 | Kohrs et al. |
| 6,245,108 B1 | * | 6/2001 | Biscup .................... 623/17.11 |
| 6,371,986 B1 | * | 4/2002 | Bagby .................... 623/17.11 |
| 6,482,233 B1 | * | 11/2002 | Aebi et al. ............... 623/17.11 |

* cited by examiner

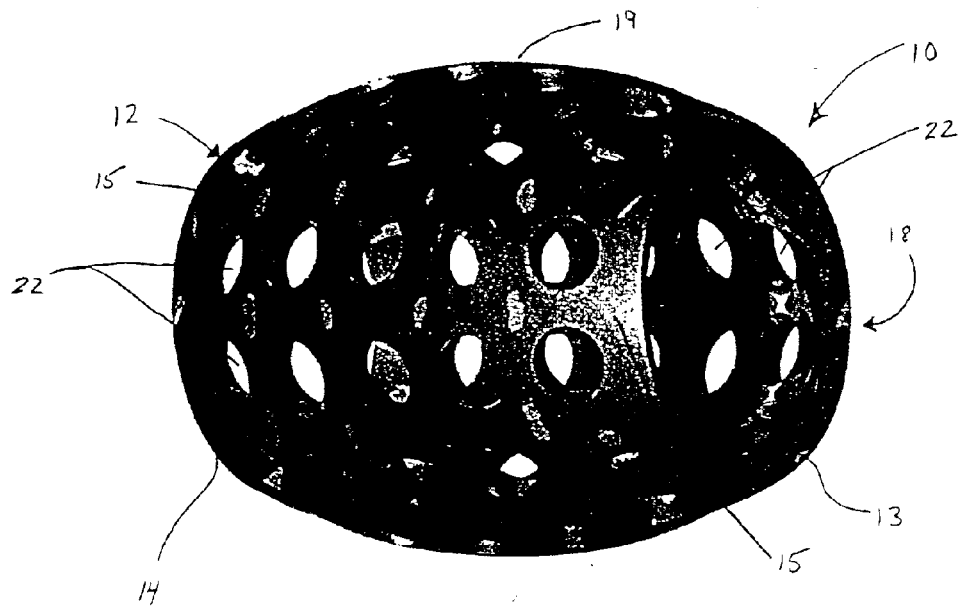
FIG. 1
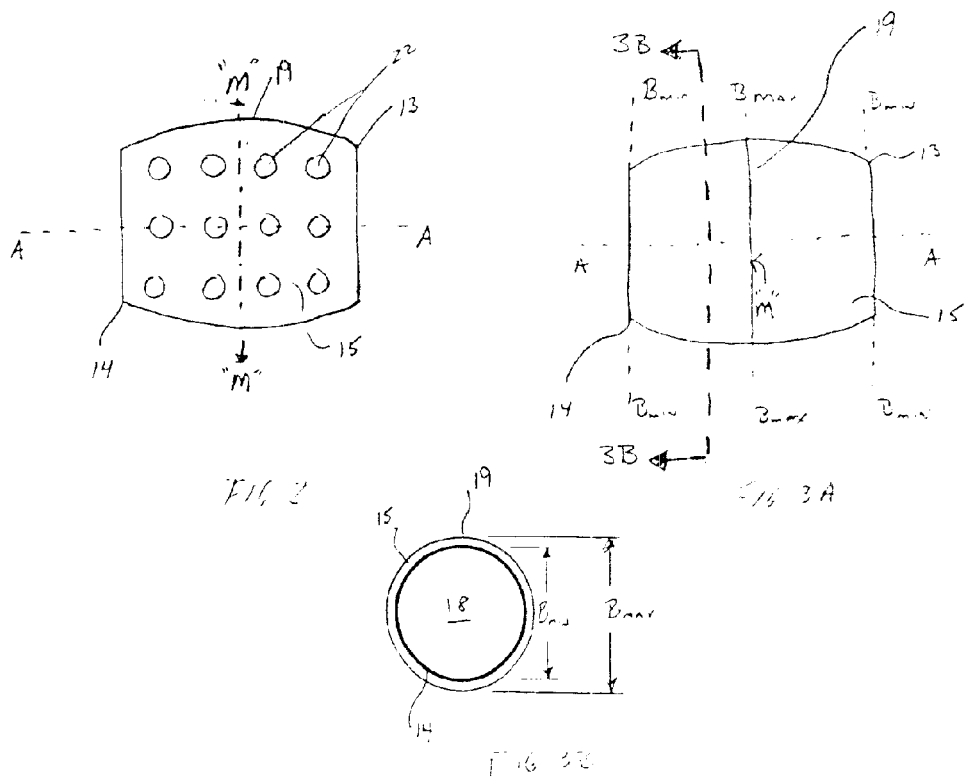

PRIOR ART
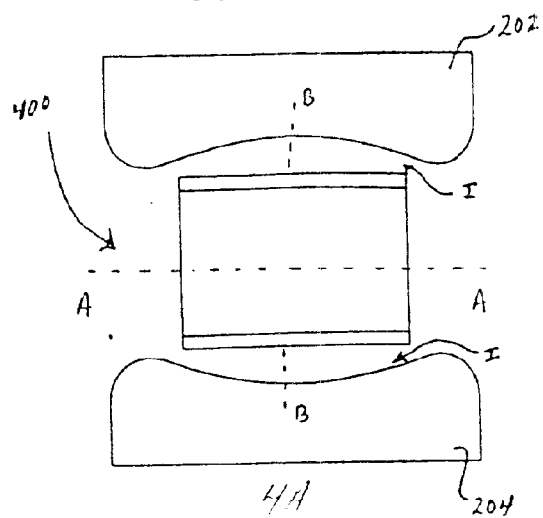
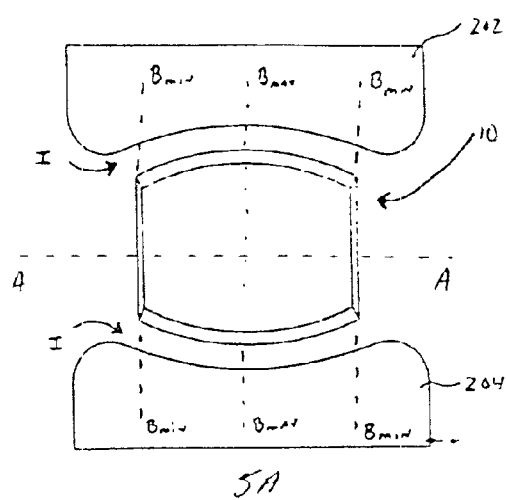
PRIOR ART
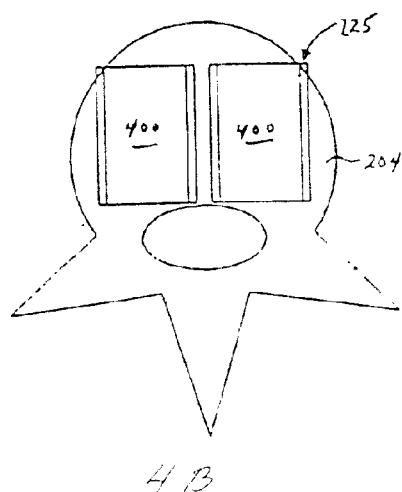
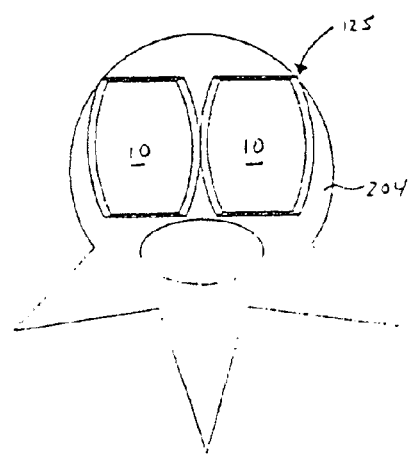

APPARATUS FOR FUSING ADJACENT BONE STRUCTURE

This application claims the benefit of the filing date of U.S. Provisional Patent Application No. 60/242,843 filed on Oct. 24, 2000, the disclosure of which is hereby incorporated herein by reference.

BACKGROUND

The present disclosure generally relates to a surgical apparatus for fusing adjacent bone structures, and, more particularly, to a barrel-shaped apparatus and method for fusing adjacent vertebrae.

TECHNICAL FIELD

The fusion of adjacent bone structures is commonly performed to provide for long-term replacement to compensate for vertebral subluxation typically caused by severe trauma to the spine, degenerative or deteriorated bone disorders, e.g., osteoporosis, abnormal curvature of the spine (scoliosis or kyphosis) and/or weak or unstable spine conditions typically caused by infections or tumors. In addition, an intervertebral disc, which is a ligamentous cushion disposed between adjacent vertebrae, may also undergo deterioration or degeneration as a result of injury, disease, tumor or other disorders. The disk shrinks or flattens leading to mechanical instability and painful disc translocations, commonly referred to as a "slipped disc" or "herniated disc".

Conventional procedures for disc surgery include partial or total excision of the injured disc portion, e.g., discectomy, and replacement of the excised disc with biologically acceptable plugs or bone wedges. The plugs are driven between adjacent vertebrae to maintain normal intervertebral spacing and to achieve, over a period of time, bony ingrowth or "fusion" with the plug and opposed vertebrae.

Alternatively, a metallic fusion cage may be inserted within a tapped bore or channel formed in the intervertebral space thereby stabilizing the vertebrae and maintaining a pre-defined intervertebral space. A pair of fusion cages may also be implanted within the intervertebral space. After a period of time, the soft cancellous bone of the surrounding vertebral bone structures infiltrates the cage through a series of apertures in the cage wall and unites with bone growth inducing substances disposed within an internal cavity to eventually form a solid fusion of the adjacent vertebrae.

SUMMARY

The present disclosure relates to a threadless, generally barrel-shaped fusion implant apparatus for facilitating fusion of adjacent bone structures. The apparatus includes an implant member which is positioned between adjacent opposed bone structures. The implant member defines a longitudinal axis and first and second longitudinal ends and has an outer wall which is dimensioned to engage the opposed bone structures upon positioning therebetween in supporting relation therewith. Preferably, the outer wall defines an internal cavity for the reception of bone growth inducing substances and includes a plurality of apertures which extend therethrough in communication with the internal cavity to permit fusion of vertebral bone tissue. The implant member also includes an intermediate portion which defines a cross-sectional dimension transverse to the longitudinal axis which is greater than the respective, corresponding cross-sectional dimensions of the first and second longitudinal ends of the implant member. Preferably, the implant member is symmetrically arranged about its medial axis to provide the general, barrel-shape or appearance.

The barrel-shaped fusion cage is configured for stable insertion within a space between adjacent vertebrae. The fusion cage may include at least one concave wall portion to facilitate lateral or side-by-side insertion with a second cage between adjacent vertebrae.

The present disclosure also relates to a method for fusing adjacent vertebrae which includes the steps of: 1) providing a threadless implant member which defines a longitudinal axis and first and second longitudinal ends, and has a cross-sectional dimension transverse to the longitudinal axis greater than the respective corresponding cross-sectional dimensions of the first and second longitudinal ends of the implant member; 2) accessing the intervertebral space defined between adjacent vertebrae; 3) advancing the implant member within the intervertebral space such that the first and second longitudinal ends are adjacent respective anterior and posterior sections of the adjacent vertebrae; and 4) permitting bone growth into contacting surfaces of the implant member to facilitate fusion of the adjacent vertebrae.

BRIEF DESCRIPTION OF THE DRAWINGS

FIG. 1 is a perspective view of a fusion cage according to the present disclosure;

FIG. 2 is a side view of the fusion cage shown in FIG. 1;

FIG. 3A is a side view of the fusion cage of FIG. 1 illustrating a bulge positioned along a medial axis "m";

FIG. 3B is a cross-sectional view of the fusion cage taken along section line 3B—3B of FIG. 3A;

FIG. 4A is a lateral view illustrating a pair of cylindrically-shaped prior art fusion implants positioned within the intervertebral space for fusion of adjacent vertebrae;

FIG. 4B is a top view showing a side-by-side orientation of two prior art cylindrically-shaped fusion cages between two adjacent vertebrae;

FIG. 5A is a lateral view showing the placement of the fusion cage of FIG. 1 between two adjacent vertebrae;

FIG. 5B is a top view showing a pair of fusion implants according to the present disclosure positioned within the intervertebral space for fusion of adjacent vertebrae;

DETAILED DESCRIPTION

Figure 6A:
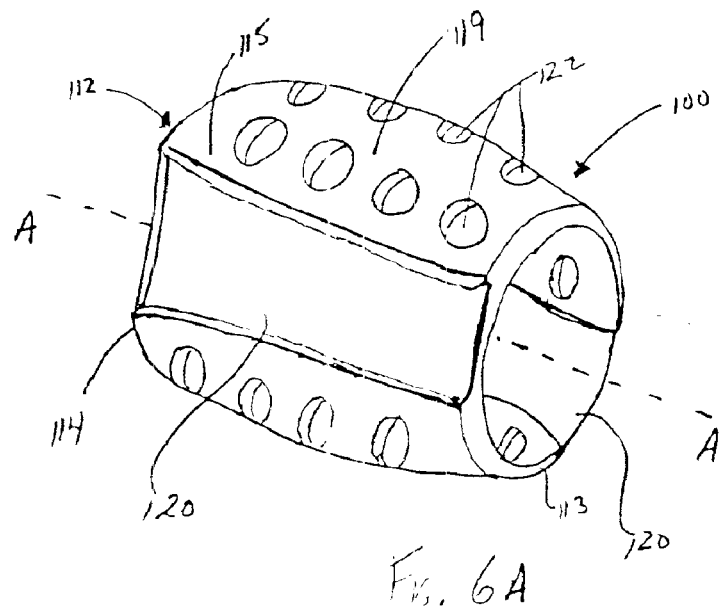
FIG. 6A is a perspective view of an alternate embodiment of the fusion cage according to the present disclosure.

Referring now to the drawings in which like reference numerals identify similar or identical elements throughout the several views, FIGS. 1–3 illustrate one embodiment of the fusion cage implant according to the present disclosure. Fusion implant 10 includes a generally elongated body 12 having a proximal end 13 and a distal end 14. In the drawings and in the description which follows, the term "proximal", as is traditional, will refer to the end of the cage 10 which is closer to the surgeon, while the term "distal" will refer to the end which is further from the surgeon. Preferably, cage 10 is fabricated from a suitable biocompatible rigid material such as titanium and/or alloys of titanium, stainless steel, ceramic materials or rigid polymeric materials. Moreover, it is envisioned that cage 10 is sufficient in strength to at least partially replace the supporting function of an intervertebral disc, i.e., to maintain adjacent vertebrae in desired spaced relation, during healing and fusion. Cage 10 is preferably provided in various lengths ranging from about 24 mm to about 28 mm for example.

As best shown in FIGS. 1, 2 and 3A, the body 12 of cage 10 includes an outer wall 15 which encloses an inner cavity 18 defined within the interior of the cage body 12. Inner cavity 18 accommodates bony ingrowth substances which induce the soft cancellous bone surrounding the vertebrae to grow inwardly towards the contact surfaces of the fusion cage 10 to stabilize the cage 10 between two adjacent vertebrae 202, 204 (FIG. 5A). Outer wall 15 is generally barrel-shaped along a longitudinal axis "A" which extends from proximal end 13 to distal end 14 (FIG. 2) and includes a bulge 19 generally positioned midway therebetween. As explained in more detail below, it is envisioned that the barrel-like shape of cage 10 increases the overall strength and load sharing capacity of the cage 10, tends to reduce "stiffness" which has been associated with other prior art designs and allows more bone graft substances to be packed into the augmented internal volume of the cage 10 which it is believed will further enhance bone fusion. It is also envisioned that this configuration provides a greater surface area of the implant so as to facilitate contacting engagement and support of the implant with the adjacent vertebrae 202, 204 (FIG. 5A).

As best shown in FIGS. 3A and 3B, the major dimension of "B" along longitudinal axis "A" varies from a minimum dimension "$B_{min}$" proximate the ends 13, 14 of cage body 12 to a bulge section 19 having a maximum dimension "$B_{max}$" generally disposed midway between ends 13, 14 along a medial transverse axis "m". More specifically, body 12 of cage 10 is symmetrically arranged about medial transverse axis "m" whereby the maximum diameter or cross-sectioned dimension $B_{max}$ extends about or adjacent to the medial transverse axis "m" and progressively decreases to the proximal and distal ends 13, 14. Preferably, the maximum diameter or dimension "$B_{max}$" ranges from about 12 mm to about 20 mm and the minimum diameter or dimension "$B_{min}$" ranges from about 13 mm to about 19 mm. In preferred embodiment, the maximum diameter is 17.5 mm and the minimum diameter is 16 mm. The length is 21 mm. Other dimensions are also contemplated.

As can be appreciated, this gives cage 10 its barrel-like or bulge-like appearance. It is envisioned that dimensioning the cage 10 in this fashion has several distinct advantages: 1) the barrel-like cage is an inherently stronger pressure vessel than a simple cylinder design, i.e., the barrel-like cage has a higher compressive strength, exhibits greater resistance to fatigue and possesses a higher yield load; 2) the barrel-like shape promotes a better anatomical fit between adjacent vertebrae 202, 204 in both the transverse plane (Compare FIG. 4B with FIG. 5B) and the sagittal plane (Compare FIG. 4A with FIG. 5A); 3) the low profile ends 13, 14 facilitate insertion of the cage 10 and allow two cages 10 to be placed side-by-side with reduced overhang 125 outside the periphery of the vertebral bodies 202 (Compare FIG. 4B with FIG. 5B); 4) the center bulge 19 enhances retention of the cage 10 once positioned between the vertebral bodies 202, 204; and 5) the barrel-like shape of the cage 10 results in an increase in the internal volume of the cage 10 which accommodates additional bone growth inducing substances and enables more bone to grow into the cage 10, thus enhancing bone-to-cage fusion. The barrel cage also exhibits a higher expulsion load, i.e., the force required to eject the cage from the intervertebral space.

With reference to FIGS. 1 and 2, the surface of outer wall 15 is preferably non-threaded or threadless. The term "threadless" is defined herein to mean that the outer wall 15 is devoid of any threads which would require rotation of the cage 10 upon positioning between the adjacent vertebrae 202, 204. It is envisioned that the surface of outer wall 15 may be coated with a variety of different materials which facilitate insertion of the cage 10 and enhance retention of the cage 10 within the pre-drilled cavity "I".

As stated above, it is also envisioned that cage 10 can be dimensioned such that cage 10 is generally symmetrical about axis "A", i.e., front-to-end symmetry, which will permit insertion of the cage 10 from either the proximal or distal end 13, 14, respectively.

As best shown in FIGS. 1 and 2, a plurality of apertures 22 extend through outer wall 15 of cage body 12 and preferably promote immediate bone to bone contact between the vertebral bodies 202, 204 and the bone inducing substances packed within the internal cavity 18 of the cage body 12. Such arrangement of apertures 22 is disclosed in commonly assigned U.S. Pat. Nos. 4,961,740 and 5,026,373, the contents of which are hereby incorporated by reference. Apertures 22 are preferably substantially the same in dimension although it is envisioned that the dimensions of the apertures 22 may vary to provide for more or less bone-to-bone contact depending upon a particular purpose.

Preferably, apertures 22 are oriented such that when the cage 10 is inserted between vertebrae, a majority of apertures 22 contact the upper and lower vertebral bone structures 202, 204 to encourage bony ingrowth through cage body 12 from the vertebral bone structures 202, 204.

FIG. 6A shows an alternate embodiment of the fusion cage 100. More particularly, outer wall 115 of cage body 112 includes at least one side cut-out or concave wall portion 120 which extends parallel to longitudinal axis "A" along outer wall 115 generally from the proximal end 113 to the distal end 114. Preferably, two side cut-outs 120 are disposed along outer wall 115 in diametrically opposing relation to one another to reduce the effective dimension or diameter of cage 100 transversally relative to longitudinal axis "A". In either case, the disposition of the side cut-out(s) 120 enhance the low profile features of the present disclosure and facilitate insertion of the cage 100 between the adjacent vertebral bodies 202, 204. Side cut-outs 120 of cage 112 preferably do not include apertures 122 in order to prevent growth of disc material which might interfere with the overall bone fusing process as will be discussed.

Figure 6B:
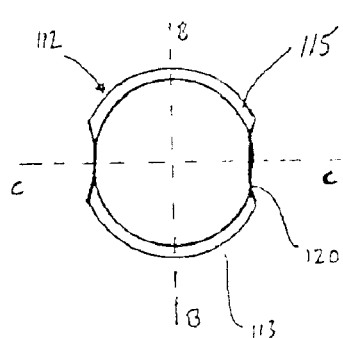
FIG. 6B is a end view of the fusion cage of FIG. 6A.

Preferably and as shown in FIGS. 6A and 6B, side cut-outs 120 of body 112 provide a generally elliptical configuration or appearance to cage 100 defining a major dimension "B" which is greater than a minor dimension "C". It is envisioned that this configuration provides a greater surface area of the implant so as to facilitate contacting engagement and support of the implant with the adjacent vertebrae 202, 204. Other dimensions are also contemplated. Preferably, the side cut-outs 120 are disposed along the minor axis "C" to enhance the low profile features of cage 100 and facilitate insertion.

Figure 6C:
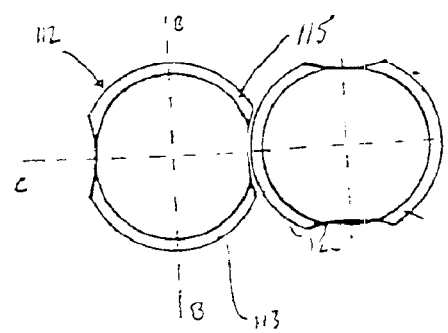
FIG. 6C is a view illustrating a pair of the implants of FIG. 6A inserted within an intervertebral space.

As can be appreciated, the low profile ends 113, 114 and the side cut-outs 120 facilitate insertion of the cage 100 and allow two cages 100, 100 to be placed side-by-side with a reduced overhang 125 outside the periphery of the vertebral bodies 202, 204 as illustrated in FIG. 6CB.

Figure 7A:
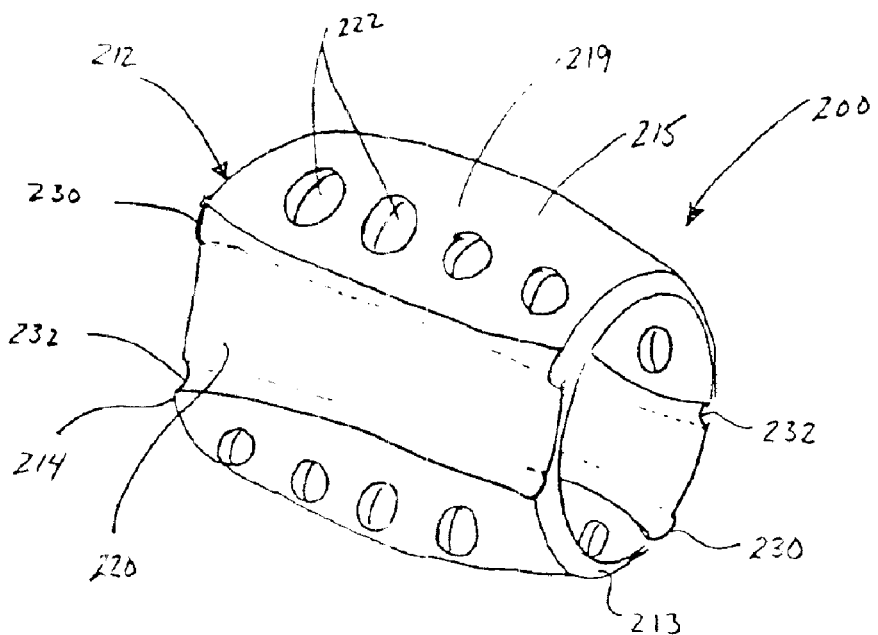
FIG. 7A is a perspective view of an alternate embodiment of the fusion cage according to the present disclosure.
Figure 7B:
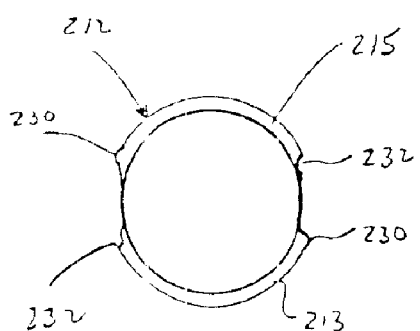
FIG. 7B is a end view of the fusion cage of FIG. 7A.

FIGS. 7A and 7B show another embodiment of the fusion cage 200. More particularly, outer wall 215 of cage body 212 includes at least one side cut-out or concave wall portion 220 which extends parallel to longitudinal axis "A" along outer wall 215 generally from the proximal end 213 to the distal end 214. Preferably, the side cut-out 220 includes at least one mechanical interface, e.g., a tongue 230, which is designed to cooperate with a corresponding mechanical interface, e.g., a groove 232, disposed on a second implant member 200 to unite two implant members 200, 200 in lateral side-by-side relation between adjacent vertebral bodies 202, 204. It is envisioned that side cut-out 220 can be dimensioned to include both a tongue 230 and a groove 232 interface disposed on opposite edges thereof which mechanically engage corresponding tongue 230 and groove 232 interfaces disposed on a second implant member 200.

As can be appreciated, implant 200 can also be dimensioned to include diametrically-opposing side cut-outs 220 each having tongue 230 and groove 232 interfaces oppositely oriented on respective edges thereof to facilitate insertion and mechanical engagement of the two implant members 200, 200 during insertion. It is envisioned that other mechanical interfaces may also be employed along the side cut-outs 220 to unite the two implants 200 during insertion, e.g., dovetail, mortise and tenon, etc.

The present disclosure also relates to a method of inserting a threadless, barrel-like fusion cage 10 into an intervertebral space "I" defined between adjacent vertebrae 202, 204. The method discussed hereinafter will generally relate to an open antero-lateral approach for spinal fusion implant insertion. However, as can be appreciated, other spinal implant procedures are also contemplated, e.g., posterior, direct anterior, etc . . . . Laparoscopic approaches are also envisioned.

Initially, one lateral side of an intervertebral space "I" between the two vertebral bodies 202, 204 is accessed utilizing appropriate retractors (not shown) to expose the anterior vertebral surface. Thereafter, the retractor is inserted within the intervertebral space "I" from an antero-lateral or oblique position with relation to the vertebral bodies 202, 204. Such an approach provides advantages with regard to avoiding vessels and ligaments.

Upon insertion of the retractor, the vertebral bodies 202, 204 are distracted whereby the retractor becomes firmly lodged within the intervertebral space "I". A drilling instrument is now utilized to prepare the disc space and vertebral bodies 202, 204 for insertion of the fusion cage 10. Preferably, the cutting depth of drilling instrument can be readily adjusted to correspond to the length of the fusion cage 10. As can be appreciated, as the drilling instrument is advanced into the intervertebral space "I", the surrounding soft tissue is sheared and the bone of the adjacent vertebrae 202, 204 is cut thereby forming a bore which extends into the adjacent vertebrae 202, 204.

The fusion cage 10 of FIG. 1 is then packed with bone growth inducing substances as in conventional in the art and then mounted on an insertion instrument (not shown) and driven between the adjacent vertebral bodies 202, 204. As mentioned above, it is envisioned that the low profile proximal and distal ends, 13 and 14, respectively, along with the center bulge 19 facilitate insertion and retention of the cage 10. Moreover, the low profile ends 13 and 14 of cage body 12 allow two cages to be placed closer together decreasing the likelihood of cage 10 overhang.

Cage 10 is then released from the mounting instrument which is subsequently removed from the disc area.

Thereafter, a second lateral side of the intervertebral space "I" is accessed and the above-described process is repeated to insert a second cage 10 in lateral side-by-side relation as shown in FIG. 5B. As appreciated, the cages 10 are arranged such that the cages 10, 10 reside in adjacent side-by-side relation.

As can be appreciated, fusion cages 10 form struts across the intervertebral space "I" to maintain the adjacent vertebrae 202, 204 in appropriate spaced relation during the fusion process. Over a period of time, the adjacent vertebral tissue communicates through apertures 22 within cages 10, 10 to form a solid fusion. It is envisioned that the barrel-like shape of each fusion cage 10 is inherently stronger that a cylinder-shaped fusion cage and provides a better anatomical fit between adjacent vertebrae 202, 204. For example and as best shown a comparison of FIGS. 4B and 5B, the prior art cylindrically-shaped fusion cages 100, 100 when positioned in side-by-side relation tend to overhang the intervertebral space "I" at point 225 wherein the barrel-like fusion cages 10, 10 when positioned in the same manner have a reduced overhang 125 thus providing a better anatomical fit within the intervertebral space "I".

The same procedure is followed in connection with insertion of the implants 100 and 200 of FIGS. 6A, 6B [and 7A, 7B], respectively. For example and with respect to the implant 100 of FIGS. 6A and 6B, upon insertion the two cages 100, 100 are arranged such that respective side cut-out portions 120 of each cage 100 are disposed in lateral side-by-side relation and not in contact with the adjacent vertebral bodies 202, 204. Alternatively, the cages 10 may be positioned such that the curved body of one cage is received within the side cut 120 of the other cage to further reduce the profile of implanted cages as depicted in FIG. 6C. As indicted above, side cut-out portions 120 are devoid of apertures 122 thereby permitting only direct bone growth or passage through the apertures 122 of the cage body portion contacting the adjacent vertebrae 202, 204.

With respect to implant 200 of FIGS. 7A and 7B, the two cages 200, 200 are arranged in the same manner as described above with respect to implant 100 with the exception that the two implants 200, 200 are dimensioned to mechanically engage one another upon insertion. More particularly and as described above, upon insertion the tongue 230 and groove 232 interface of the side cut-out 220 of the first implant 200 is dimensioned to slidingly engage a corresponding tongue 230 and groove 232 interface of the side cut-out 220 of the second implant 200 to secure the two implants 200, 200 in lateral side-by-side relation between adjacent vertebral bodies 202, 204. As mentioned above, other mechanical interfaces can be employed to mechanically unite the two implants 200, 200 once disposed between adjacent vertebral bodies 202, 204.

From the foregoing and with reference to the various figure drawings, those skilled in the art will appreciate that certain modifications can also be made to the present disclosure without departing from the scope of the same. For example, it is envisioned that a series of apertures could be drilled at one end of the cage 10 which would allow a surgeon to use a smaller tang and smaller drill thereby preserving more of the posterior elements of the spine during the operation.

While the above description contains many specifics, these specifics should not be construed as limitations on the scope of the disclosure, but merely as exemplifications of preferred embodiments thereof. Those skilled in the art will envision other modifications within the scope and spirit of the claims appended hereto.

What is claimed is:

1. A fusion implant apparatus for facilitating fusion of adjacent bone structures, which comprises:

a threadless implant member for positioning between adjacent opposed bone structures, the implant member defining a longitudinal axis and first and second longitudinal ends, said longitudinal axis being bisected by a transverse orthogonal axis, wherein said implant member is longer along said longitudinal axis than along said orthogonal axis, the implant member further defining an outer wall dimensioned to engage the opposed bone structures upon positioning therebetween in supporting relation therewith, the outer wall defining an internal cavity for reception of bone growth inducing substances and including a plurality of apertures extending therethrough in communication with the internal cavity to permit fusion of vertebral bone tissue, the implant member having an arcuate intermediate portion defining a cross-sectional dimension transverse to the longitudinal axis greater than respective cross-sectional dimensions of the first and second longitudinal ends of the implant member, wherein the implant member defines a substantially circular cross-section.

2. The fusion implant apparatus according to claim 1 wherein the cross-sectional dimension of the implant member progressively increases in an arc from each of the first and second ends toward the intermediate portion.

3. The fusion implant apparatus according to claim 2 wherein the cross-sectional dimensions of the first and second ends are substantially equal.

4. The fusion implant apparatus according to claim 3 wherein the implant member defines a medial transverse axis equidistally disposed between the first and second longitudinal ends and wherein the implant member is symmetrically arranged about the medial transverse axis.

5. The fusion implant apparatus according to claim 1 wherein the outer wall of the implant member includes at least one concave wall portion extending along the longitudinal axis.

6. The fusion implant apparatus according to claim 5 wherein the outer wall includes diametrically opposed concave wall portions.

7. The fusion implant apparatus according to claim 1 wherein the implant member is dimensioned and configured for insertion between adjacent vertebrae.

8. A fusion implant apparatus for facilitating fusion of adjacent vertebrae, which comprises:

an implant member dimensioned for positioning between adjacent vertebrae to support the adjacent vertebrae in spaced relation, the implant member defining a longitudinal axis and first and second longitudinal ends, said longitudinal axis being bisected by a transverse orthogonal axis, wherein said implant member is longer along said longitudinal axis than along said orthogonal axis, the implant member further defining an outer wall dimensioned to engage the adjacent vertebrae upon positioning therebetween, the outer wall dimensioned to engage the adjacent vertebrae upon positioning therebetween, the outer wall defining an internal cavity for reception of bone growth inducing substances, the outer wall being devoid of any threads, the implant member having an arcuate intermediate portion defining a cross-sectional dimension transverse to the longitudinal axis greater than respective corresponding cross-sectional dimensions of the first and second longitudinal ends of the implant member, the outer wall having a plurality of apertures extending therethrough in communication with the internal cavity to permit fusion of vertebral bone tissue, wherein the implant member defines a substantially circular cross-section.

9. The fusion implant apparatus according to claim 8 wherein the cross-sectional dimension of the implant member progressively increases in an arc from each of the first and second ends toward the intermediate portion.

10. The fusion implant apparatus according to claim 8 wherein the outer wall of the implant member includes at least one concave wall surface portion extending along the longitudinal axis.

11. A method for fusing adjacent vertebrae, comprising the steps of:

providing a threadless implant member defining a longitudinal axis and first and second longitudinal ends, said longitudinal axis being bisected by a transverse orthogonal axis, wherein said implant member is longer along said longitudinal axis than along said orthogonal axis, the implant member having an arcuate intermediate portion defining a cross-sectional dimension transverse to the longitudinal axis greater than respective corresponding cross-sectional dimensions of the first and second longitudinal ends of the implant member, wherein the implant member defines a substantially circular cross-section;

accessing the intervertebral space defined between adjacent vertebrae;

advancing the implant member within the intervertebral space such that the first and second longitudinal ends are adjacent respective anterior and posterior sections of the adjacent vertebrae; and permitting bone growth into contacting surfaces of the implant member to facilitate fusion of the adjacent vertebrae.

12. The method of claim 11 wherein the implant member includes an exterior wall defining an internal cavity and having apertures extending therethrough and further including the step of permitting bony tissue of the adjacent vertebrae to grow through the apertures to communicate with bone growth inducing substances disposed within the internal cavity.

13. A fusion implant apparatus for facilitating fusion of adjacent bone structures, which comprises:

a threadless implant member for positioning between adjacent opposed bone structures, the implant member defining a longitudinal axis and first and second longitudinal ends, one of such ends being open, said longitudinal axis being bisected by a transverse orthogonal axis, wherein said implant member is longer along said longitudinal axis than along said orthogonal axis, the implant member further defining an outer wall dimensioned to engage the opposed bone structures upon positioning therebetween in supporting relation therewith, the outer wall defining an internal cavity for reception of bone growth inducing substances and including a plurality of apertures extending therethrough in communication with the internal cavity to permit fusion of vertebral bone tissue, said open end being larger than any one of said apertures, the implant member having an intermediate portion defining a cross-sectional dimension transverse to the longitudinal axis greater than respective cross-sectional dimensions of the first and second longitudinal ends of the implant member, wherein the implant member defines a substantially circular cross-section.

14. The fusion implant apparatus according to claim 13 wherein the implant member defines a medial transverse axis equidistally disposed between the first and second longitudinal ends and wherein the implant member is symmetrically arranged about the medial transverse axis.

15. A fusion implant apparatus for facilitating fusion of adjacent vertebrae, which comprises:
   an implant member dimensioned for positioning between adjacent vertebrae to support the adjacent vertebrae in spaced relation, the implant member defining a longitudinal axis and first and second longitudinal ends, one of such ends being open, said longitudinal axis being bisected by a transverse orthogonal axis, wherein said implant member is longer along said longitudinal axis than along said orthogonal axis, the implant member further defining an outer wall dimensioned to engage the adjacent vertebrae upon positioning therebetween, the outer wall dimensioned to engage the adjacent vertebrae upon positioning therebetween, the outer wall defining an internal cavity for reception of bone growth inducing substances, the outer wall being devoid of any threads, the implant member having an intermediate portion defining a cross-sectional dimension transverse to the longitudinal axis greater than respective corresponding cross-sectional dimensions of the first and second longitudinal ends of the implant member, the outer wall having a plurality of apertures extending therethrough in communication with the internal cavity to permit fusion of vertebral bone tissue, said open end being larger than any one of said apertures, wherein the implant member defines a substantially circular cross-section.

16. The fusion implant apparatus according to claim 15 wherein the cross-sectional dimension of the implant member progressively increases from each of the first and second ends toward the intermediate portion.

17. A method for fusing adjacent vertebrae, comprising the steps of:
   providing a threadless implant member defining a longitudinal axis and first and second longitudinal ends, one of such ends being open, said longitudinal axis being bisected by a transverse orthogonal axis, wherein said implant member is longer along said longitudinal axis than along said orthogonal axis, the implant member further defining, the implant member having an intermediate portion defining a cross-sectional dimension transverse to the longitudinal axis greater than respective corresponding cross-sectional dimensions of the first and second longitudinal ends of the implant member, wherein the implant member defines a substantially circular cross-section;
   accessing the intervertebral space defined between adjacent vertebrae;
   advancing the implant member within the intervertebral space such that the first and second longitudinal ends are adjacent respective anterior and posterior sections of the adjacent vertebrae; and
   permitting bone growth into contacting surfaces of the implant member to facilitate fusion of the adjacent vertebrae.

18. The method of claim 17 wherein the implant member includes an exterior wall defining an internal cavity and having apertures extending therethrough and further including the step of permitting bony tissue of the adjacent vertebrae to grow through the apertures to communicate with bone growth inducing substances disposed within the internal, cavity, said open end being larger than any one of said apertures.

* * * * *

UNITED STATES PATENT AND TRADEMARK OFFICE
CERTIFICATE OF CORRECTION

PATENT NO. : 6,902,581 B2
DATED : June 7, 2005
INVENTOR(S) : Jared Walkenhorst, Herb Cohen and Lance Middleton It is certified that error appears in the above-identified patent and that said Letters Patent is hereby corrected as shown below:

Title page,
Item [73], Assignee, "Kowmedica" should read -- Howmedica --.

Column 2,
Lines 48 and 53, "is a end" should read -- is an end --.

Column 3,
Line 8, insert a comma -- , -- after "mm".

Column 4,
Line 67, "FIG. 6CB" should read -- FIG. 6C --.

Column 5,
Line 49, insert the word -- the -- after the word "of".

Column 6,
Line 13, delete the word "that" and insert the word -- than --.
Line 45, delete the word "is" and insert the word -- are --.

Column 10,
Line 8, delete the words "the implant member".
Line 9, delete the words "further defining,".
Line 31, delete the comma "," after the word "internal".

Signed and Sealed this

Eighteenth Day of October, 2005

JON W. DUDAS
*Director of the United States Patent and Trademark Office*